United States Patent [19]

Gresser et al.

[11] Patent Number: 5,429,822

[45] Date of Patent: Jul. 4, 1995

[54] BIODEGRADABLE BURSTING RELEASE SYSTEM

[75] Inventors: Joseph D. Gresser, Brookline; Donald L. Wise, Belmont; Abdul G. Jimoh, Brookline, all of Mass.; Don C. Augenstein, Palo Alto, Calif.; Dean O. Kuethe, Watertown; Debra J. Trantolo, Princeton, both of Mass.

[73] Assignee: Cambridge Scientific, Inc., Belmont, Mass.

[21] Appl. No.: 852,372

[22] Filed: Mar. 13, 1992

[51] Int. Cl.[6] ................................................ A61F 2/00
[52] U.S. Cl. ................................. 424/426; 424/468; 424/476; 424/497
[58] Field of Search ............... 424/468, 426, 476, 497, 424/472, 44

[56] References Cited

U.S. PATENT DOCUMENTS

| | | | |
|---|---|---|---|
| 3,952,741 | 4/1976 | Baker | 128/260 |
| 4,147,767 | 4/1979 | Yapel, Jr. | 424/22 |
| 4,177,256 | 12/1979 | Michaels et al. | 424/22 |
| 4,344,929 | 8/1982 | Bonsen et al. | 424/44 |
| 4,348,387 | 9/1982 | Brownlee et al. | 424/178 |
| 4,351,337 | 9/1982 | Sidman | 424/426 |
| 4,439,196 | 3/1984 | Higuchi | 604/890 |
| 4,450,150 | 5/1984 | Sidman | 424/1.1 |
| 4,469,681 | 9/1984 | Brownlee et al. | 424/178 |
| 4,500,337 | 2/1985 | Young et al. | 71/67 |
| 4,564,364 | 1/1986 | Zaffaroni et al. | 604/897 |
| 4,568,559 | 2/1986 | Nuwayser et al. | 427/3 |
| 4,576,604 | 3/1986 | Guittard et al. | 604/890 |
| 4,585,652 | 4/1986 | Miller et al. | 424/83 |
| 4,590,062 | 5/1986 | Jang | 424/19 |
| 4,591,496 | 5/1986 | Cohen et al. | 424/15 |
| 4,623,588 | 11/1986 | Nuwayser et al. | 428/402.24 |
| 4,631,190 | 12/1986 | Shen et al. | 424/85 |
| 4,673,565 | 6/1987 | Di Luccio et al. | 424/443 |
| 4,698,264 | 10/1987 | Steinke | 428/402.2 |
| 4,717,566 | 1/1988 | Eckenhoff et al. | 424/438 |
| 4,722,898 | 2/1988 | Errede et al. | 435/182 |
| 4,726,951 | 2/1988 | Panoz et al. | 424/465 |
| 4,761,289 | 8/1988 | Shalati | 424/468 |
| 4,767,628 | 8/1988 | Hutchinson | 424/426 |
| 4,789,516 | 12/1988 | Lim | 264/4.32 |
| 4,810,501 | 3/1989 | Ghebre-Sellassi et al. | 424/469 |
| 4,822,339 | 4/1989 | Tran | 604/82 |
| 4,828,857 | 5/1989 | Sharma et al. | 426/285 |
| 4,837,032 | 6/1989 | Ortega | 424/469 |
| 4,847,093 | 7/1989 | Ayer et al. | 424/44 |
| 4,863,736 | 9/1989 | Azain | 424/426 |
| 5,091,185 | 2/1992 | Castillo | 424/476 |
| 5,100,669 | 3/1992 | Hyon | 424/497 |
| 5,153,002 | 10/1992 | McMullen | 424/472 |

Primary Examiner—Thurman K. Page
Assistant Examiner—William E. Benston, Jr.
Attorney, Agent, or Firm—Weingarten, Schurgin, Gagnebin & Hayes

[57] ABSTRACT

A biodegradable polymeric multiphasic release system of one or more biodegradable bursting units capable of delivering biologically active substances in a burst or pulse at predetermined times and a method for constructing those units is disclosed. The individual bursting units of the system may take the form of a biodegradable, membrane coated capsule surrounding a core material which may include an active agent. The membrane ruptures after a predetermined time upon exposure to water or bodily, or other aqueous environmental fluids. The bursting units may be used in any situation in which a controlled pulsed release of an active substance is desired. The predetermined time release of each bursting unit is controlled by the composition of the core material, the initial radius and wall thickness of the membrane and the porosity of the membrane. The core material may also contain a chemical composition which generates gas as fluid is drawn into the bursting unit thus adding an additional design variable for predetermining bursts.

8 Claims, 3 Drawing Sheets

BIODEGRADABLE BURSTING RELEASE SYSTEM

FIELD OF THE INVENTION

The present invention relates to delivery systems of biologically active substances, and more particularly to bursting release systems capable of delivering substances in a burst or pulse at predetermined times.

BACKGROUND OF THE INVENTION

There are a variety of situations in which it is advantageous to have a system for delivering biologically active substances in bursts or pulses at predetermined times without human or mechanical intervention.

For example, some hormones only exhibit their effect if they are administered in pulses. At the present time, patients and laboratory animals, in order to be administered periodic pulses of hormones, wear hormone pumps that are programmed to inject hormones at particular intervals. These pump-like devices are subject to leaks, require maintenance, and are cumbersome. By reason of their size, they are unsuitable for rats, mice and other small laboratory animals.

A small implantable, biocompatible and biodegradable system which would make the controlled administration of bioactive agents to both animals and man, easier, less painful, and less time consuming, and which additionally is less cumbersome than the portable pumps, is therefore desirable.

For example, in a classical immunization procedure, which may achieve short-term immunity, a single dose of antigen is delivered in one injection. Antigen initially is present at a high level for a short time, but is soon lost from the inoculation site. However, with repeated treatments, a strengthened immune response is evoked which may impart lasting immunity. An implantable, biocompatible and biodegradable polymeric system for immunization offers several attractive features. Such a controlled release system would deliver a second burst of antigen at a predetermined amount of time following a first burst. The second burst would elicit a secondary immune response without the need for a second or third booster vaccination.

Another example in which a controlled pulsed release of a bioactive substance would be desirable is in the distribution of pesticides on, for example farm land. In some cases, it is desirable to release some insecticides or insect pheromones in response to rain. This is desirable because many insect pests hatch shortly after rain, when fields are too wet for farmers to enter with tractors to spread pesticides. Thus, rather than apply unnecessary pesticides continuously, thereby possibly killing helpful insects and spiders, a biodegradable bursting pesticide delivery system could be spread at some time before a rain storm and used to deliver the insecticide only when needed. The individual bursting units of this system, which would release pesticides at a predetermined time after rain or exposure to water, would be much more efficient and less damaging to the environment.

Previously, long acting polymeric release devices have been developed which provide near zero order or continuous release of an active agent. The continuous or uniform release of an active agent is not ideal in many instances, such as those discussed above.

U.S. Pat. No. 4,591,496 issued to Baker, discloses a osmotic bursting dispenser having an active agent incorporated in an enclosed semipermeable container. Although several parameters which affect bursting time are discussed, no empirical or theoretical relationships are disclosed. In addition, although the dispenser is suggested for use as an implant in animals, the container materials suggested are non-biodegradable.

SUMMARY OF THE INVENTION

The invention relates to a biodegradable polymeric multiphasic release system of one or more bursting units each capable of delivering biologically active substances in a burst or pulse at a predetermined time and a method for constructing the osmotic bursting units. Each osmotic bursting unit may take the form of a biocompatible, biodegradable membrane covered polymeric capsule that ruptures after a predetermined time following exposure to bodily or other aqueous environmental fluids. The bursting unit may be used in any situation in which a controlled pulsed release of a biologically active substance is desired.

A system of multiple bursting units may be implanted subcutaneously in a mammal and used to deliver pulsed doses of a variety of bioactive agents such as hormones (including follicle stimulating hormone, somatotropin, growth hormone and LHRH), immunogens, or any of a variety of drugs, at predetermined times. The system may also be used to release insecticides, biocides, fertilizers, agrichemicals, flavors and fragrances at predetermined times.

The bursting unit may contain a long term or steady release device which provides a steady controlled release of a bioactive agent between bursts.

The predetermined time release of each bursting unit of the system is determined by the composition of the material enclosed by the membrane (the core material); the initial radius and wall thickness of the membrane, and the porosity of the membrane.

In one embodiment, a cylindrical polymeric capsule of polymeric polylactic acid (PLA) (also known as polylactide) or polymeric poly(lactic-co-glycolic) acid (PLGA) (also known as poly(lactide-co-glycolide)) is capped with a coating or film of poly(lactic/glycolic) acid (PLGA) copolymers.

The material to be encapsulated may include, in addition to the active agent, a mixture of citric acid-sodium bicarbonate and with or without an optional osmolyte such as glucose.

The system of the invention provides substantial advantages in delivering bioactive substances including maximizing the therapeutic effects of a variety of treatment regimens through controlled pulsed release of the active agent at discrete and predetermined intervals.

DESCRIPTION OF THE DRAWINGS

The invention will be more fully understood from the following detailed description taken in conjunction with the accompanying drawing in which.

Figure 1:
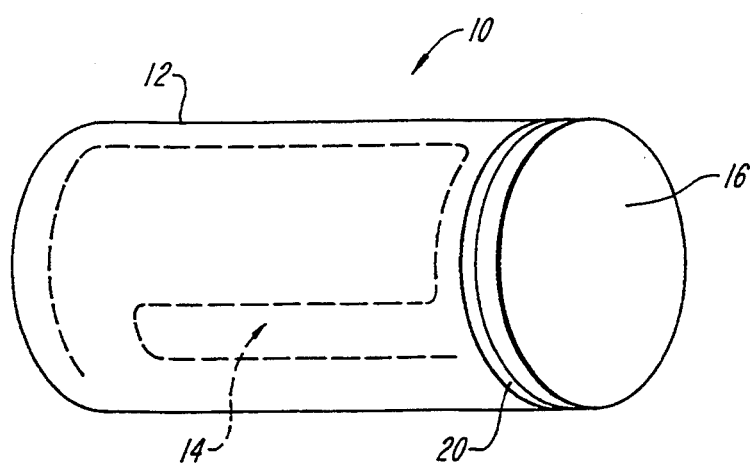
FIG. 1 is a perspective view of an embodiment of a bursting unit 10 including a biocompatible, biodegradable cylindrical open ended shell 12 filled with a bioactive agent 14. The open end of the cylindrical shell 12 is "capped" with a poly (lactic-co-glycolic) acid (PGLA) copolymer membrane 16 fastened with a medical grade adhesive 20.
Figure 3:
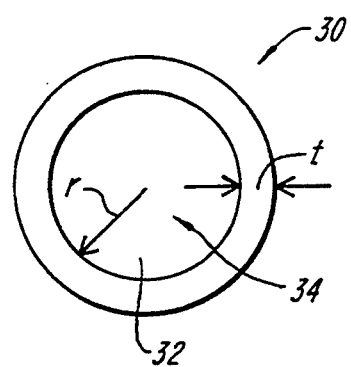
FIG. 3 is diagram of an embodiment of a spherical osmotic bursting unit in which a polymer minisphere 30 contains powdered biologically active material 32 intermixed with an associated core material 34. The minisphere has an internal radius r and a wall thickness t.
Figure 4:
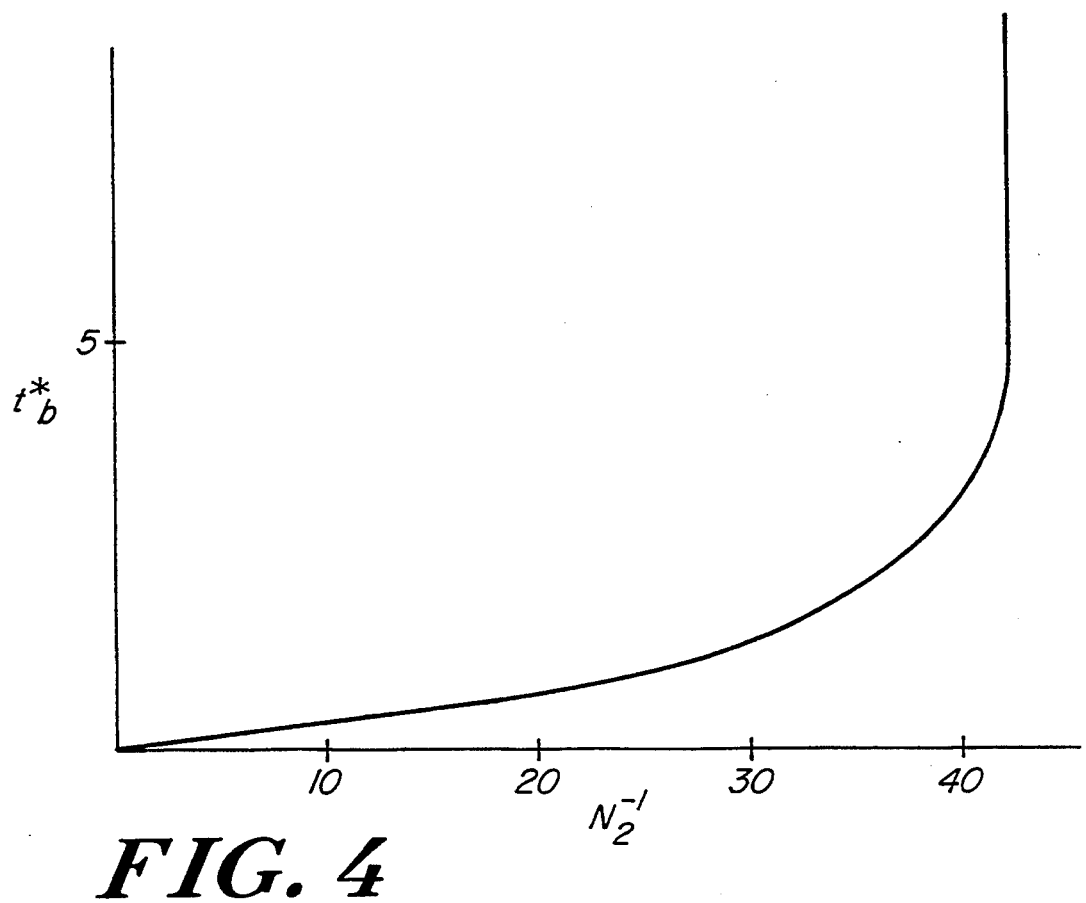
Figure 4A:
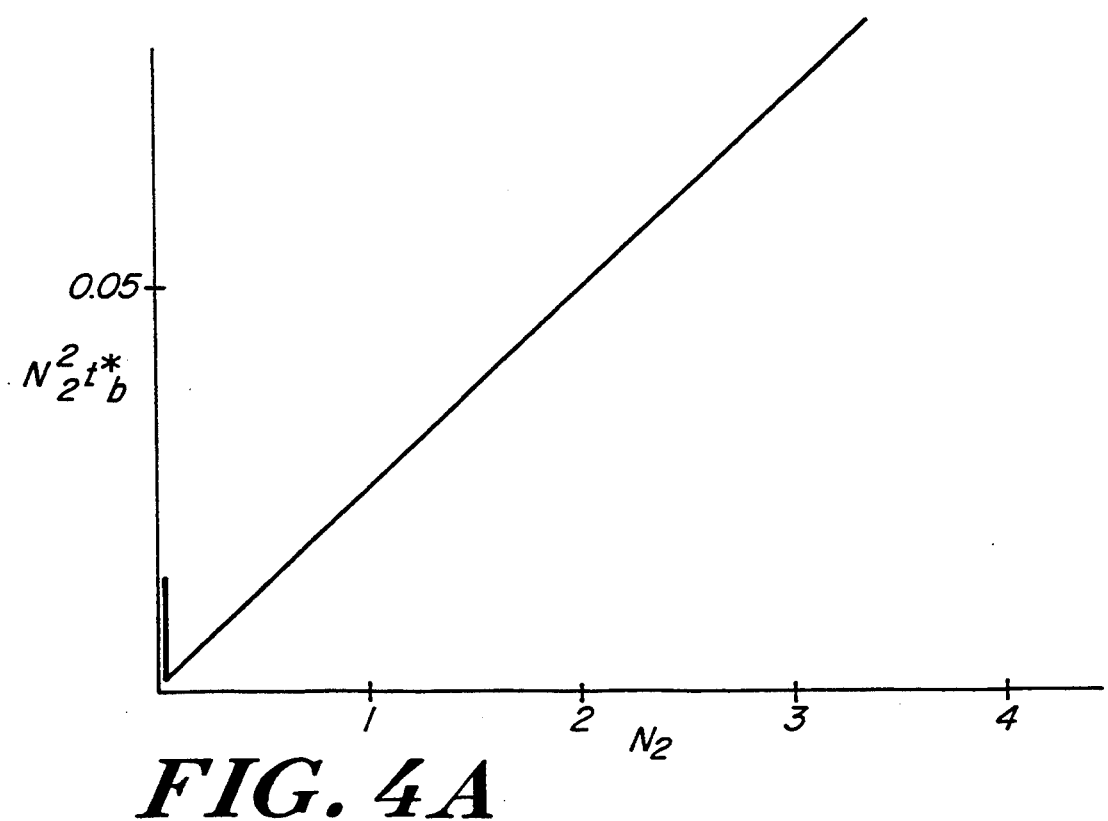
Figure 5:
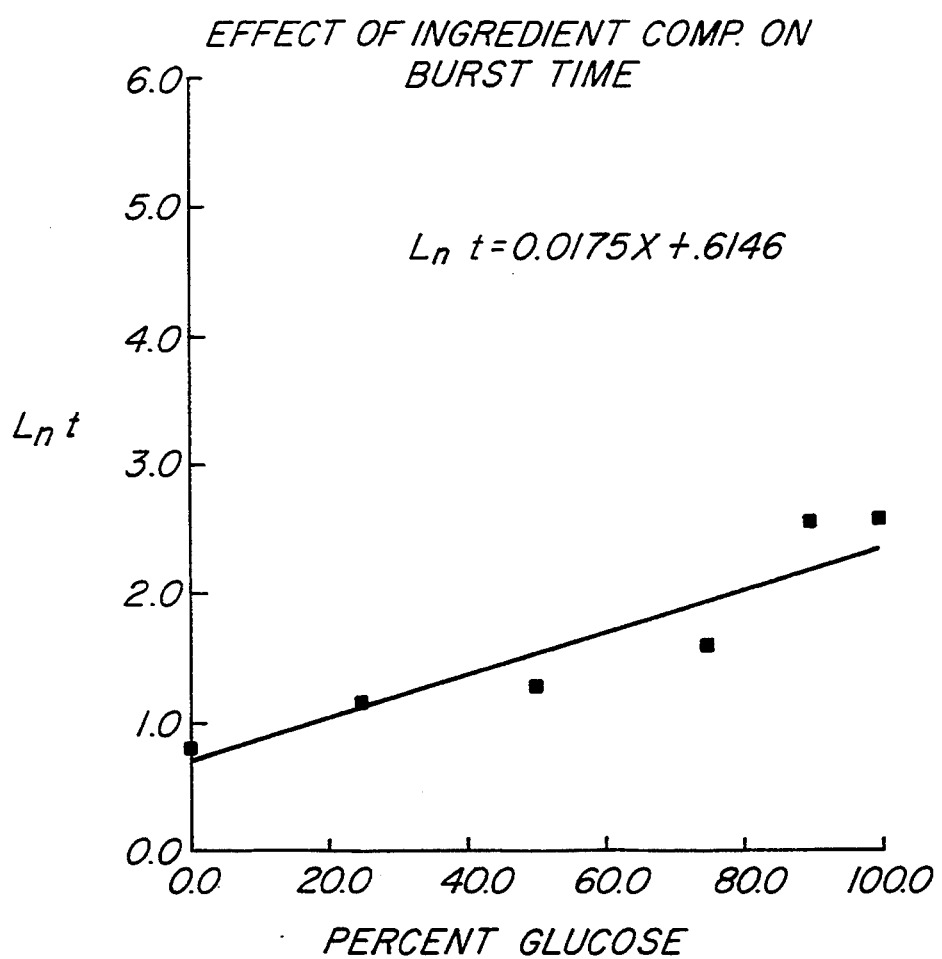

FIG. 4 is a graph showing the effect of initial wall thickness on burst time for the spherical osmotic bursting unit of FIG. 3;

FIG. 4a is a graph showing the effect initial radius on burst time for the spherical osmotic bursting unit of FIG. 3; and FIG. 5 is a graph showing the effect core composition on burst time for the bursting unit of FIG. 1.

DETAILED DESCRIPTION OF THE INVENTION

The biodegradable multiphasic release system of the invention includes one or more bursting units, each of which includes a bioactive agent which is encapsulated within a biodegradable, biocompatible polymeric membrane that ruptures and releases the bioactive material at a predetermined time following exposure to bodily or other aqueous environmental fluids. Two or more such devices may be administered or applied simultaneously and each device may be designed to burst and release its contents in a single "pulse" at a different predetermined time thereby creating a biodegradable multiphasic delivery profile of the bioactive substance.

The bursting unit may be constructed as an osmotically bursting unit, in which osmotic pressure developed within the bursting unit eventually causes the membrane of the unit to burst. The bursting unit may also be constructed as a diffusive bursting unit in which water diffusing into the bursting unit eventually causes the unit to burst. Alternatively, the bursting unit may be constructed with a gas generating material included in the core material which generates gas upon exposure to water. In this embodiment, as water is drawn into the bursting unit either by osmotic pressure or diffusion, gas is generated. The bursting unit expands due to the gas trapped within the unit until the unit bursts.

The particular physical form of the release system may vary according to the situation in which the system is used. That is, the capsule itself may act as the osmotic or diffusive membrane or a capsule which is permeable to both water and the core materials may be coated with an osmotic or diffusive membrane material. Alternatively, the core material may be formed into a tablet and coated with the osmotic or diffusive membrane material. For example, if the system is to be administered orally, coated beads, capsules, powders or tablets may be preferred. For subcutaneous or intramuscular implantation of the system, coated rods, capsules or suspended powders may be most suitable. For distribution over the surface of land, for example for insecticide or fertilizer distribution, the bursting units may preferably be spherical.

Referring to FIG. 1, in one embodiment, bursting unit 10 of the system includes a biocompatible, biodegradable cylindrical open ended shell or capsule 12 filled with a bioactive agent 14 and other carrier or core components. The cylindrical shell 12 may be formed from a poly(lactic-co-glycolic) acid copolymer (PLGA) which is frequently used in the manufacture of capsules known to the art. PLGA copolymers are biodegradable, biocompatible and exhibit moderate strength in tension, compression, and bending. In addition, PLGA copolymers have physical advantages which include hydrophobicity and pliability. Although PLGA polymers are not soluble in water, the product of their hydrolysis, lactic and glycolic acid monomers are soluble in water. The ratio of lactic acid to glycolic acid in the copolymer is varied as dictated by the specific application. The open end of the cylindrical shell 12 is "capped" with a poly(lactic-co-glycolic) acid (PGLA) copolymer membrane 16 fastened with a medical grade adhesive such as a "SILASTIC" adhesive 20. Alternatively, the capping membrane 16 may be heat or solvent welded to the cylindrical shell 12, thus avoiding the use of non-degradable adhesives. It should be noted that other biocompatible polymers, such as those fabricated from the Kreb's cycle monomers (such as fumaric acid, succinic acid, etc.) may be used, as can any number of biocompatible polymers which are used as implant materials.

Figure 2:
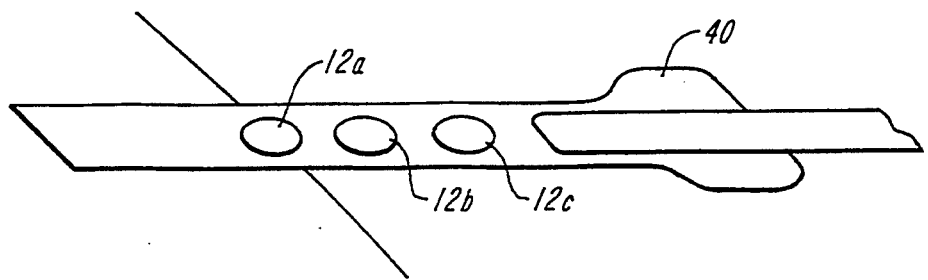
FIG. 2 is a diagram of a number of bursting units 12(a), 12(b), 12(c), each having a different bursting time shown being administered by a trochar 40.

The diameter of the cylindrical shell 12 may range from about 1-10 mm, and the length of the cylindrical shell 12 may range from about 2-10 mm. The dimensions may be adjusted to suit the particular dosage of bioactive agent required as well as the means by which the capsule is to be administered or applied. Cylindrical shells 12 or capsules are particularly suitable for subcutaneous administration via a trochar 40 (FIG. 2). In FIG. 2, a series of bursting units 12(a), 12(b), 12(c), each having a different bursting time, are shown within the trochar (40). In this example, the first capsule 12(a) is constructed to burst at time ($t_1$) while the second capsule 12(b) is constructed at time $t_2 > t_1$, and capsule 12(c) is constructed to burst to burst at time $t_3 > t_2$.

Membranes may be prepared by either evaporation of solvent from a polymer solution, as in solvent or solution casting, or from polymer melts as known in the art. In solvent based film preparations, the film thickness may be controlled by the weight of the polymer dissolved in the solvent as well as the volume of solvent used and the area to which it is confined. The solution of co-polymer and solvent may be cast onto a clean surface and the solvent allowed to evaporate. The resulting film may then be dried. Capsules may also be formed from extruded tubing of poly (lactic-co-glycolic) acid In non-solvent film preparation, the thickness of the membrane may be controlled by the temperature and pressure applied by the platens of a hydraulic press, on a given weight of polymer located on the platen. In such systems a polymer powder is formed into a thin film by the application of heat and pressure. Typically, PLA and PLGA films may be created by the application of heat and pressure until the polymer experiences a temperature of between 86° C. and 170° C. and an applied pressure of between 1000 and 7000 psi. The films are then allowed to cool under pressure. Non-solvent based films may be preferable because no solvent is required. In addition, in a solvent-free system, additives such as sodium chloride, glucose, or compatible plasticizers may be incorporated to enhance the permeability of the film. It is not possible to include additives such as sodium chloride or glucose in a solvent based film preparation since these additives are not soluble in many of the solvents; soluble plasticizers may be used in conjunction with solvent based films.

The core material of the bursting unit preferably includes at least one bioactive agent which is to be administered, and a carrier, for example an osmolyte, such as glucose. In addition, the carrier may include a sodium bicarbonate-citric acid mixture. The concentration of sodium bicarbonate-citric acid mixture in the core material may range from 0%–100% with the concentration of glucose of the core material conversely ranging from 100%–0%.

The proper physical design of the biodegradable membrane coated polymeric capsule is essential in controlling the specific time at which the burst or pulse which releases the bioactive ingredient from the capsule. Factors important in controlling the time at which a capsule bursts and releases its ingredients are: 1) the physical size of the bursting unit, 2) the porosity and permeability as determined by polymer composition of the membrane or film (for example as determined by the copolymer ratio of glycolic acid to lactic acid), and the inclusion of additives such as plasticizers, 3) the thickness of the membrane, and 4) core composition.

Spherical Bursting Unit Having an Elastic, Osmotic, Membrane

A bursting unit constructed with an osmotic, elastic, membrane (for example, one constructed of 100% lactic acid polymer), will be considered first.

A mathematical model which incorporates the effects of the strength of the membrane material, the size of the bursting unit, the membrane thickness, and the permeability of the membrane has been developed for a spherical osmotic, elastic, bursting unit provides a first approximation for constructing a bursting unit which releases its bioactive agent at the desired time. Referring to FIG. 3, a polymer minisphere 30 as shown contains powdered biologically active material 32 intermixed with an associated core material 34. The core material 34 may include a biologically compatible osmolyte such as glucose, whose function is to dissolve in water to form a solution of high osmotic strength. The biopolymeric wall of the minisphere 30 is permeable to water but not permeable to the biologically active material 32 or the core material 34. Upon immersion in water or tissue fluids, the water activity gradient across the sphere wall causes water to diffuse into the sphere so that solution volume steadily increases within the sphere. As solution volume increases, the sphere walls begin to stretch to accommodate this increased volume. However, with proper choice of parameter values, solution pressure within the sphere ultimately ruptures the sphere so that contents are released. Clearly, by using spheres with various parameter values, a variety of times for capsule rupture may be selected. Thus, a predetermined sequence of bursts or pulses of biologically active material may be released.

The solubility of the core material 34 is assumed to be such that a saturated core material solution of osmotic pressure ($P_o$) is formed upon exposure to water, and the solution remains saturated by the reserve of solid core material, and at osmotic strength ($P_o$), until the sphere rupture occurs. For this analysis the osmotic pressure assumed is that of glucose, which appears to be an excellent osmolyte. A saturated solution of glucose at 37° C. can sustain an osmotic pressure differential ($P_o$) of $1.4 \times 10^8$ dynes/cm², against water across a semipermeable membrane. The osmotic pressure contribution by the small amount of biologically active material is assumed to be negligible. It is also assumed that there are no concentration gradients in the sphere interior. That is, all of the solution is of one osmotic strength ($P_o$), and all water transfer resistance is in the sphere wall.

For the purpose of the model, the wall material is assumed to be impermeable to the core material and the wall thickness is low compared to sphere diameter so that effects of wall curvature are minimal. As water penetrates the sphere wall, it is assumed that the sphere expands elastically until the yield stress is reached. That is, it is assumed that the elastic modulus of the sphere material does not change with strain. The permeability of sphere wall to water and impermeability to core material are also assumed not to be altered by stress, strain or time. It is also assumed that the time constant for degradation of the biodegradable polymer will be much larger than the time to burst.

The rate of expansion of the volume (V) sphere is given by the equation:

$$dV/dt = D \frac{A}{l}(P_o - p) \quad \text{Equation 1}$$

where (D) is the dialysis permeability of the sphere material, (A) is the surface area of the sphere, (l) is the wall thickness of the sphere material at time (t), (p) is the internal pressure in the sphere at time (t) and ($P_o$) is the osmotic pressure of the contents of the sphere. The sphere bursts when the yield stress (Y) is reached in a membrane having a Young's modulus of (M), and the radius of the sphere has expanded to the bursting radius $r_b$, from an initial radius $r_o$.

$$Y = M \frac{r_b - r_o}{r_o} \quad \text{Equation 2}$$

Therefore, since the volume of capsule material is a constant, and the thickness (l) of the wall at time (t) is related to the thickness of the wall initially ($l_o$), by the square of the ratio of the initial radius ($r_o$) to the radius (r) at time (t), the two equations may be rewritten as:

$$\frac{dr}{dt} = 2DM\left(\frac{P_o r^2}{2M l_o r_o^2} - \frac{1}{r_o} + \frac{1}{r}\right) \quad \text{Equation 3}$$

Defining $N_2 = (P_o r_o)/(2M l_o)$ and $N_1 = (Y/M)$, if the parameters are chosen such that:

$$N_2 = \frac{P_o r_o}{2M l_o} \geq 4/27 \quad \text{Equation 4}$$

then the sphere will rupture when:

$$r = r_o\left(\frac{Y}{M} + 1\right) \quad \text{Equation 5}$$

This occurs at time ($t_b$) which is given by the equation:

$$t_b = \left(\frac{r_o^2}{2DM}\right) t_b^* \quad \text{Equation 6}$$

where ($t_b^*$) is dimensionless time given by the equation:

$$t_b^* = \frac{1}{3\sqrt{2(\alpha^2 + \beta^2)} + 1}\left[(\alpha + \beta)\ln\frac{\alpha + 1 - \alpha - \beta}{1 - \alpha - \beta} - \right. \quad \text{Equation 7}$$

-continued $$\frac{\alpha+\beta}{2}\ln\left(\frac{(\varkappa 1+1)^2+(\varkappa 1+1)(\alpha+\beta)+\alpha^2+\beta^2+\alpha\beta}{1+\alpha+\beta+\beta^2-\alpha\beta}\right)-$$

$$\frac{\sqrt{3}(\alpha^2+\beta^2)}{(\alpha-\beta)}\arctan\left(\frac{\sqrt{3}(\alpha-\beta)}{2(\varkappa 1+1)+\alpha+\beta}\right)-$$

$$\arctan\left(\frac{\sqrt{3}(\alpha-\beta)}{2+\alpha+\beta}\right)\Bigg], \text{ where } \alpha =$$

$$\left[\frac{1}{\varkappa 2}\sqrt{\frac{1}{4}-\frac{1}{27\varkappa 2}}-\frac{1}{2}\right]^{\frac{1}{3}} \text{ and } \beta =$$

$$-\left[\frac{1}{\varkappa 2}\left(\sqrt{\frac{1}{4}-\frac{1}{27\varkappa 2}}+\frac{1}{2}\right)\right]^{\frac{1}{3}}.$$

FIG. 4 is a graph of the dimensionless time ($t_b^*$) plotted against ($1/N_2$) and shows the effect of initial wall thickness on burst time ($t_b^*$). FIG. 4a is a graph of ($N_2^2 t_b^*$) against $N_2$ and shows the effect initial radius ($r_o$) on burst time ($t_b$). Thus, with the remaining variables held constant, a bursting unit may be created to burst at a predetermined time simply by adjusting the value of the initial radius of the bursting unit or the initial thickness of the wall of the bursting unit.

For example, to make a bursting unit which bursts after 12 hours, using a material having a yield stress (Y)=$5\times 10^7$ Pa; a Young's modulus (M) of $2\times 10^9$ Pa; a dialysis permeability (D) of $10^{-20}m^2S^{-1}Pa^{-1}$; and incorporating a saturated glucose solution having an osmotic pressure ($P_o$) of $1.2\times 10^7$ Pa; ($t_b^*$) is chosen (FIG. 5) to equal 0.695 and $N_2^{-1}$ to equal 20, leading to an initial radius ($r_o$) of 1.58 mm and an initial wall thickness ($l_o$) of 0.095 mm.

Thus by choosing a variety of bursting units having various wall thicknesses and/or initial radii, bioactive agents could be released periodically. Such an osmotically bursting system may be used, for example in vaccine inoculation. The bioactive agent is, in this example, an immunizing agent and the bursting units are designed to achieve release profiles that will elicit the optimal immunological or therapeutic response when implanted subcutaneously. In this novel system, one or more of the implants could be designed to release antigen slowly over a period of several days post-implant, while one or more different implants are designed to administer a second booster inoculation, to insure long term immunity, at a predetermined time, such as one or more weeks after implantation. An implanted vaccine of this kind would present the immunogen in such a manner as to enhance the response of the immune system, and will generally provide the immune response equal to three or more separate injections in a one-injection dose form.

Spherical Bursting Unit Having a Non-Elastic, Non-Osmotic, Membrane

At the other extreme, capsules may be constructed of a polymer which permits water to be transferred by diffusion only and which is plastic; that is, non-elastic. For example, by increasing the glycolic acid concentration in a copolymer membrane of poly (lactic-co-glycolic) acid, the membrane becomes increasingly diffusion limited and non-elastic.

With this type of membrane, the bursting unit expands many times that of a bursting unit made from an elastic membrane, without bursting because of membrane creep (the plastic behavior of the membrane). In a bursting unit made of this type of copolymer, the membrane stretches until flaws in the membrane stretch into holes large enough to permit the core material to exit the bursting unit. For example, a 75%/25% poly (lactic-co-glycolic) acid membrane creeps at a rate of 0.02% to 0.5% per second at stresses between 3 and 15 MPa. It should also be noted that identical membranes may exhibit creep rates which differ by a factor of 25 or more.

In this mathematical model, it is assumed that the core material includes anhydrous glucose, or similar material, which will absorb water strongly and yet not swell appreciably. Water is assumed to diffuse at a constant rate into the capsule and the rate is controlled by the thickness of the wall and the size of the capsule.

The capsule, in this example includes a composition added to the core material of the bursting unit which will generate gas when water is drawn into the bursting unit. For example, a gas generating mixture which is particularly useful is a 1:3 molar combination of citric acid and sodium bicarbonate. As water enters the bursting unit, the sodium bicarbonate and citric acid react generating carbon dioxide ($CO_2$). The $CO_2$ generated creates a gas pressure and the time to bursting can be adjusted by varying the amount of citric acid-sodium bicarbonate mixture present in the bursting unit relative to the amount of the other core materials.

For the purposes of the model it is assumed that the membrane creeps perfectly (i.e. the gas within the membrane is not compressed) and the capsule breaks after it swells to between 1.5 and 3 times its initial radius. The rate of influx of water into a spherical capsule of radius (r) and wall thickness (l) is given by the equation:

$$Q=(Df)A(Pw)/l \qquad 8$$

where (Df) is the diffusion coefficient; (A) is the area of the capsule; and (Pw) is the partial pressure of water. If the anhydrous glucose (termed compound B) absorbs a portion (b) of its own volume without swelling and if it occupies a fraction (F) of the capsule volume, the capsule does not swell until time (t)>($t_1$) where ($t_1$) is given by the equation:

$$(t_1)=bF(4\pi/3)r_o^3/Q \qquad 9$$

If the capsule contains a gas generating mixture (termed compound A) that releases (a) parts of gas per volume of water absorbed, after time ($t_1$) the volume expands at a rate:

$$dV/dt=aQ \qquad 10$$

Since the thickness of the wall changes, but the volume of the wall material remains constant, the thickness of the wall at any time is a function of the radius of the sphere:

$$l=l_o(r_o^2/r^2) \qquad 11$$

where $l_o$ is the initial wall thickness. Solving for the rate of expansion of the radius:

$$dr/dt = a(Df)(Pw)r^2/l_o r^2 \qquad 12$$

Defining dimensionless time (t*) by:

$$t^* = \frac{(Df)(Pw)t}{r_o l_o} \qquad \text{Equation 13}$$

and dimensionless radius (r*) as $$r^* = r/r_o \qquad 14$$

Then, $$dr^*/dt^* = ar^{*2} \qquad 15$$

This can be integrated to determine the dimensionless time $t_2^*$ it takes for the capsule to burst after it begins to swell.

$$t_2^* = \frac{1}{a}\left(1 - \left(\frac{1}{(x,y)}\right)\right) \qquad \text{Equation 16}$$

where (x,y) indicates the ranges of sizes within which the capsule may rupture.

Since, from Equation 9, $$t_1^* = bF/3 \qquad 17$$

then $$t_b^* = t_1^* + t_2^* = (bF/3) + (1/a)(1-1)(x,y)) \qquad 18$$

Since the range of sizes at which the capsule may burst is from x to y times the initial radius, it is desired to keep $t_2^*$ small with respect to $t_1^*$. This can be accomplished by: 1) choosing a substance B that absorbs a large portion of its volume b in water without expanding; 2) having a large portion F of the capsule filled with substance B (provided there is still enough substance A to break the capsule in a rapid expansion); and/or 3) using a substance A that releases a great proportion a of gas for an absorbed volume of water.

Cylindrical Bursting Unit Having a Non-Elastic, Non-Osmotic, Membrane

The effect of using a citric acid-sodium bicarbonate/glucose core on burst time of a cylindrical capsule is shown in FIG. 5. The data indicate, for this capsule of 70/30 PGLA material, that the burst time increases as the citric acid-sodium bicarbonate concentration decreases. For the particular capsules used, the data can be fit by an expression of the form:

$$\ln(t_b) = c_1(\text{concentration of core material}) + c_2 \qquad 19$$

where $c_1$ and $c_2$ are constants. For example, the burst time, in hours, for a 2 mm diameter 70/30 PLGA capsule having a 40 micron wall thickness with a citric acid-sodium bicarbonate/glucose mixture is given by the equation:

$$\ln(t_b) = 0.01746(\% \text{ of glucose}) + 0.6146 \qquad 20$$

with a correlation coefficient of 91.25%. It is important to note that since the evolution of gas by the mixture is determined by the amount of water present within the bursting unit, the citric acid-sodium bicarbonate and glucose (a hygroscopic mixture) should be protected from moisture during storage and formulation.

The relationship of equation (9) is supported by in vitro studies employing films fabricated from poly (lactide-co-glycolide) which had been synthesized from 70% of d,1-lactide and 30% glycolide. Films having thicknesses of 10, 40, and 80 microns were fixed to capsules. The film diameters were 2, 3, and 9 mm.

Data of Tables 1 and 2 reveal the correlations whereby burst times may be controlled by judicious choice of the parameter values of 1) film thickness, 2) film or capsule diameter, and 3) core composition. The entries in table 2 listing the burst times with a 0% glucose concentration in the core material (i.e., 100% sodium bicarbonate/citric acid) indicate a cluster of values in the range 100 to 113 minutes. Although 4 of the 9 times are considerably outside this range, it should be noted that these shorter times are extrapolated values. That is, these experiments did not include a core composition of 0% glucose. Thus, at a core composition of 100% sodium bicarbonate/citric acid, burst times of about 100 minutes may be anticipated for films from 10 to 80 microns thick, and having diameters from 2 to 9 mm. For core compositions of 100% glucose (i.e. bursting due to diffusion pressure only) burst times are seen to increase with film diameter.

Another correlation which is apparent from examination of Tables 1 and 2 is that the slope ($\lambda$) of the linear regression for the relationship:

$$\ln(t_b) = (\lambda)(\text{Glucose concentration}) + \mu \qquad 21$$

increases with increasing film diameter and with decreasing film thickness.

The experimental data for cylindrical capsules also indicate that burst time is approximately a linear function of film diameter. This relationship can be deduced from the data presented in Table 3 which relates burst time to both film diameter (for devices such as pictured in FIG. 1) to both film diameter and core composition for a series of 40 micron films prepared from 70/30 PLGA.

The linear relationship is made evident by dividing burst times for a given core composition by the corresponding film diameters. These values, which are reported in Table 4, as well as are the standard deviations, may be summarized in the linear relationships given in Table 5. It would be noted that the percent standard deviations from the linear relationships vary between 6.4 to a maximum of 18%.

An example of a specific situation in which the system of the invention can be used is in the area of domestic livestock reproduction management. Genetically engineered Bovine Follicle Stimulating Hormone (b-FSH) is currently used to superovulate cows. Superovulation typically requires multiple injections. Therefore, an implantable biodegradable multiphasic controlled release system for b-FSH would be a very attractive alternative to individual injection since a stock breeder would not need to incur the cost associated with multiple injections.

Cows undergoing such treatment are injected with two injections per day for four days. This usually results in a yield of 10–12 ova, of which 50%–80% are viable, i.e. suitable for fertilization and implantation in surrogate cows. As a practical matter, a breeder wishing to treat one cow will be required to administer 8 injections (1 cow×2 injections/day×4 days) which is clearly impractical in a commercial setting. In contrast, the biodegradable multiphasic release system of the invention has been implemented which, when implanted, is designed to provide a pulsed release of the hormone as often as every 4–8 hours. Since this requires only the initial injection to the cow to implant the system subcutaneously, the cost savings are significant. The biodegradable multiphasic release system of the invention provides an equivalent of 12–24 injections over a 4 day period, requiring much less b-FSH since the delivery of the hormone is at maximum efficiency.

Table 6 discloses the parameters of the osmotic bursting units used to induce superovulation in cows. The osmotic bursting units were formed using 40μ 70/30 PLGA film to seal the end of a 2 or 3 mm long PLGA capsule. The core contained p-FSH with varying compositions of sodium bicarbonate-citric acid and glucose to adjust the burst times. The sodium bicarbonate-citric acid and glucose compositions were selected to provide burst times of 2, 4, 8, 12, 24, 36, 48, and 96 hours.

Surgery was performed to examine the reproductive activities of each cow one week after implantation. The results of the first round are presented in Table 7. It should be noted that two cows (Nos. 828 and 825) received a total of eight capsules, each containing 8 or 4 mg. of FSH. One cow (No. 806) was implanted with a steady release device fabricated by the extrusion of a PLGA/FSH mixture in the form of a rod. One cow (no. 824) received both steady and pulsed release implants.

It can be seen from Table 7 that the cows that were treated with the pulsed and steady release of FSH had a total of 11 ovulation points each, while the cow treated with both pulsed and steady release of FSH had 16 ovulation points. A normal non-treated cow typically has 1 or 2 ovulation points. The estrus cycle of cow number 828 was missed, resulting in no ovulation points. Thus, it can be seen that the use of bursting units containing p-FSH produces increased ovulation without requiring additional injections.

It is also possible to encapsulate a constant or steady release device along with the core material within a bursting unit. With such a device it is possible to provide a series of steady release doses which will cover an extended period of time.

These and other examples of the concept of the invention illustrated above are intended by way of example and the actual scope of the invention is to be determined solely from the following claims.

TABLE 1

LINEAR REGRESSION ANALYSIS OF BURST TIME/CORE COMPOSITION CORRELATION FOR VARIOUS FILM DIAMETERS AND THICKNESSES

| Diameter mm | Thickness micron | $\text{Ln}(t) =$ | Correlation Coefficient |
|---|---|---|---|
| 9 | 40 | $= 4.6540 + 0.0448G^*$ | 0.9939 |
| 3 | 10 | $= 2.1449 + 0.0509G$ | 0.9678 |
|   | 40 | $= 4.6112 + 0.0304G$ | 0.9677 |
|   |    | $= 1.3576 + 0.0450G$ | 0.7393 |
|   | 80 | $= 4.6618 + 0.0076G$ | 0.9902 |
|   |    | $= 3.6277 + 0.0256G$ | 0.9843 |
| 2 | 10 | $= 3.2382 + 0.0364G$ | 0.9706 |
|   | 40 | $= 4.6216 + 0.0219G$ | 0.9216 |
|   |    | $= 4.7263 + 0.0176G$ | 0.9242 |

*$G$ = percent glucose in core mixtures

TABLE 2

BURST TIMES IN MINUTES FOR 0% AND 100% GLUCOSE IN CORE AND SLOPES OF LINEAR REGRESSIONS

| Diameter mm | Thickness, microns | | | | | | | | |
|---|---|---|---|---|---|---|---|---|---|
| | 10 micro | | | 40 microns | | | 80 microns | | |
| | 0% | 100% | slope | 0% | 100% | slope | 0% | 100% | slope |
| 2 | 26* | 971 | 0.0364 | 102 | 908 | 0.0219 | | | |
|   |     |     |        | 113 | 656 | 0.0179 | | | |
| 3 | 9   | 1387| 0.0509 | 101 | 2103| 0.0304 | 106 | 226 | 0.0076 |
|   |     |     |        | 4   | 350 | 0.0450 | 38  | 487 | 0.0256 |
| 9 |     |     |        | 105 | 9265| 0.0448 | | | |

*burst time given in minutes

TABLE 3

BURST TIME AS A FUNCTION OF FILM DIAMETER AND CORE COMPOSITION FOR A SERIES OF 40 MICRON THICK, 70/30 PLGA FILMS

| Percent Glucose | Diameter | | |
|---|---|---|---|
| | 9 mm | 3 mm | 2 mm |
| 25 | — | 4.1 hrs | 3.2 hrs |
| 50 | 12 hrs | 4.5 | 3.7 |
| 75 | 56 | 16.4 | 5.2 |
| 100 | 168 | 44.7 | 24 |

TABLE 4

LINEAR DEPENDENCE OF BURST TIME ON FILM DIAMETER: (RATIO OF BURST TIME TO FILM DIAMETER)

| Percent Glucose | Ratio of Burst Time to Film Diameter | | | | |
|---|---|---|---|---|---|
| | 9 mm | 3 mm | 2 mm | mean ± SD | (% SD) |
| 25 | — | 1.35 | 1.60 | 1.48 ± 0.13 | 8.5% |
| 50 | 1.33 | 1.50 | 1.85 | 1.56 ± 0.22 | 13.9% |
| 75 | 6.22 | 5.47 | 2.60* | 5.85 ± 0.37 | 6.4% |
| 100 | 8.7 | 14.9 | 12.0 | 15.2 ± 2.7 | 18.0% |

*Omitted from calculation of mean
SD = standard deviation

TABLE 5

DEPENDENCE OF BURST TIME ON FILM DIAMETER FOR VARIOUS CORE COMPOSITIONS

| % Glucose | Burst Time, hrs. |
|---|---|
| 25 | $t = 1.48\ \text{d}\ (\pm 8.5\%)$ |
| 50 | $t = 1.56\ \text{d}\ (\pm 13.9\%)$ |
| 75 | $t = 5.85\ \text{d}\ (\pm 6.4\%)$ |
| 100 | $t = 15.2\ \text{d}\ (\pm 18.0\%)$ |

TABLE 6

DESCRIPTION OF SAMPLES FOR COW TESTS

| Capsule Type | Ingredient composition | Wt. FSH (mg) | Expected Burst Time (hrs) |
|---|---|---|---|
| 2 mm | 0/100 S-C/G | 2(8); 3(4) | 2 |

TABLE 6-continued

DESCRIPTION OF SAMPLES FOR COW TESTS

| Capsule Type | Ingredient composition | Wt. FSH (mg) | Expected Burst Time (hrs) |
|---|---|---|---|
| 2 mm/3 mm | 75/25 S-C/G | 2(8); 3(4) | 4 |
| 2 mm | 80/20 S-C/G | 2(8); 3(4) | 8 |
| 2 mm | 90/10 S-C/G | 2(8); 3(4) | 13 |
| 3 mm | 60/40 S/G | 2(8); 3(4) | 21 |
| 3 mm | 40/60 S/G | 2(8); 3(4) | 33 |
| 3 mm | 80/20 S/G | 2(8); 3(4) | 53 |
| 2 mm | 100/0 SC/G | 2(8); 3(4) | 96 |

Legend

S-C/G = NaHCO$_3$-Citric Acid/Glucose;

S/G = NaHCO$_3$/Glucose (no citric acid)

2(8) = 2 capsules each containing 8 mg FSH;

3(4) = 3 capsules each containing 4 mg FSH

TABLE 7

IMPLANT RESULTS FROM FIRST ROUND

| Cow # | Detailed Description | # of Capsules | Ovulation | URF | CL Points | CA |
|---|---|---|---|---|---|---|
| 828 | Pulsed, 8 mg dosage | 8 | R.O | 6 | 0 | 1 |
| | | | L.O | 5 | 0 | 1 |
| 825 | Pulsed, 4 mg dosage | 8 | R.5 | 4 | 0 | 0 |
| | | | L.6 | 1 | 0 | 0 |
| 806 | Steady, 30 mg dosage | 30% loading | R.2 | 1 | 0 | 0 |
| | | | L.9 | 4 | 0 | 0 |
| 824 | Pulsed + Steady (4 mg Pulsed, 30 mg Steady) | 8 | R.8 | 3 | 1 | 0 |
| | | | L.8 | 1 | 0 | 0 |

Legend
OP = Ovulation points,
URF = Unruptured follicles
CL = Corpora Lutia,
CA = Corpora Albicans
R = Right,
L = Left

What is claimed is:

1. A biodegradable multiphasic delivery system, comprising at least one biodegradable, biocompatible bursting unit, said bursting unit comprising a polymer membrane encapsulating a core material, said core material comprising a predetermined quantity of at least one substance that reacts with water to form a predetermined amount of gas, said polymer membrane permitting a predetermined volume of water, from an environment into which said bursting unit is placed, to enter said bursting unit to react with said at least one substance to form said predetermined amount of gas to cause said bursting unit to rupture, thereby releasing said core material in a single pulse from said bursting unit into said environment.

2. The system of claim 1 wherein said membrane is selected from the group consisting of polylactic acid (PLA), poly (lactic-co-glycolic) acid (PLGA) copolymers, polymers of Kreb's cycle monomers and biocompatible implant polymers.

3. The system of claim 3 wherein said at least one substance is a sodium bicarbonate-citric acid mixture.

4. The system of claim 1, wherein said core material further comprises an osmolyte such as glucose.

5. The system of claim 1, wherein said core material further comprises a drug.

6. The system of claim 5, wherein said drug comprises a hormone.

7. The system of claim 6, wherein said hormone is selected from the group comprising follicle stimulating hormone, growth hormone, somatotropin and LHRH.

8. The system of claim 5, wherein said drug comprises an immunogen used in vaccine preparations.

* * * * *

UNITED STATES PATENT AND TRADEMARK OFFICE
CERTIFICATE OF CORRECTION

PATENT NO. : 5,429,822
DATED : July 4, 1995
INVENTOR(S) : Joseph D. Gresser, et al.

It is certified that error appears in the above-indentified patent and that said Letters Patent is hereby corrected as shown below:

Column 1, line 65, "4,591,496" should read --3,952,741--.

Column 6, line 43, in Equation 4, " $\geqq$ " should read -- $\geq$ --.

Column 9, line 10, " $r^*=r/r_o$ " should read
-- 6X21    $r^*=r/r_o$ --.

Column 14, line 33, "claim 3" should read --claim 1--.

Column 14, line 42, "group comprising" should read --group consisting of--.

Signed and Sealed this

Thirteenth Day of August, 1996

Attest:

BRUCE LEHMAN

Attesting Officer            Commissioner of Patents and Trademarks